United States Patent [19]

Smith et al.

[11] Patent Number: 5,414,106

[45] Date of Patent: May 9, 1995

[54] PROCESS FOR RECOVERING DIMETHYL TEREPHTHALATE

[75] Inventors: Brad L. Smith; Gary E. Wilkins, both of Wilmington, N.C.

[73] Assignee: Hoechst Celanese Corporation, Somerville, N.J.

[21] Appl. No.: 195,669

[22] Filed: Feb. 14, 1994

[51] Int. Cl.⁶ .............................................. C07C 67/48
[52] U.S. Cl. .......................................... 560/78; 560/96
[58] Field of Search .................................. 560/78, 96

[56] References Cited

U.S. PATENT DOCUMENTS

| | | | |
|---|---|---|---|
| 2,828,330 | 3/1958 | Sinn et al. | |
| 2,884,443 | 4/1959 | Siggel | 260/475 |
| 2,905,708 | 9/1959 | Peterson et al. | 260/475 |
| 3,037,050 | 5/1962 | Heisenberg | 260/475 |
| 3,148,208 | 9/1964 | Siggel | 260/475 |
| 3,321,510 | 5/1967 | Lotz et al. | 260/475 |
| 3,402,195 | 9/1968 | Barna | 260/475 |
| 3,488,298 | 1/1970 | Barkey et al. | 260/2.3 |
| 3,686,276 | 8/1972 | Slockett | 260/475 |
| 3,907,868 | 9/1975 | Currie et al. | 260/475 |
| 4,013,519 | 3/1977 | Hoppert et al. | 203/33 |
| 4,078,143 | 3/1978 | Malik et al. | 560/78 |
| 4,118,582 | 10/1978 | Walker | 560/96 |
| 4,163,860 | 8/1979 | Delattre et al. | 560/96 |
| 4,410,449 | 1/1983 | Diessel | 502/24 |
| 4,464,477 | 8/1984 | Bünger et al. | 502/24 |
| 4,578,502 | 3/1986 | Cudmore | 560/79 |
| 4,609,634 | 9/1986 | King, Jr. | 502/24 |
| 5,051,528 | 9/1991 | Naujokas et al. | 560/78 |

OTHER PUBLICATIONS

Chemical Engineers' Handbook Fifth Edition, McGraw-Hill Book Company New York, N.Y., 1973 pp. 21-3-29.

Primary Examiner—José G. Dees
Assistant Examiner—Samuel Barts
Attorney, Agent, or Firm—R. H. Hammer, III

[57] ABSTRACT

A process for recovering dimethyl terephthalate (DMT) is disclosed. The process includes the steps of: (a) providing a DMT stream, the DMT stream including DMT, catalyst, and ethylene glycol; (b) adding a solvent to the DMT stream, the solvent being immiscible with water and miscible with DMT; (c) adding water to the DMT stream; and (d) forming two phases, a first phase of the solvent and DMT, and a second phase of water, ethylene glycol, and catalyst.

7 Claims, 2 Drawing Sheets

PROCESS FOR RECOVERING DIMETHYL TEREPHTHALATE

FIELD OF THE INVENTION

This invention is directed to a process for the recovery of dimethyl terephthalate (DMT), ethylene glycol (EG), and catalyst from scrap polyethylene terephthalate (PET) and PET production waste.

BACKGROUND OF THE INVENTION

Scrap polyethylene terephthalate (PET) and PET production waste are often landfilled. Landfilling of these materials represents, among other things, a loss of raw material, and a potential ecological problem, if improperly landfilled. Accordingly, an economical process for the recycling of these materials is desirable.

The recycling of scrap PET and PET production waste, in general, is known. The materials can be reacted with methanol, i.e., "methanolysis", to produce dimethyl terephthalate (DMT) For example, see U.S. Pat. Nos. 2,884,443; 3,037,050; 3,148,208; 3,321,510; 3,488,298; 3,907,868; 4,163,860; 4,578,502; and 5,051,528. PET scrap can be reacted with ethylene glycol, i.e. "glycolysis", to produce bis-(2-hydroxyethyl) terephthalate (BHET), a PET monomer. For example, see U.S. Patent No. 4,078,143, column 1. PET scrap can be melted and reformed without depolymerization. Additionally, there are known methods by which catalyst can be removed from PET production waste. For example, see U.S. Pat. Nos. 4,013,519 and 4,118,582.

Two problems arise with the recycling of scrap PET and PET production waste: the effective separation of ethylene glycol (EG) and DMT, and the removal of the polycondensation catalysts. Separation of EG from DMT prior to DMT purification is important because EG and DMT react to form BHET. Removal of the catalyst is important because it is an unwanted contaminant in DMT.

Accordingly, there is a need for a process in which the ethylene glycol and catalyst can be efficiently removed from DMT in a recovery process.

SUMMARY OF THE INVENTION

A process for recovering dimethyl terephthalate (DMT) is disclosed. The process includes the steps of: (a) providing a DMT stream, the DMT stream including DMT, catalyst, and ethylene glycol; (b) adding a solvent to the DMT stream, the solvent being immiscible with water and miscible with DMT; (c) adding water to the DMT stream; and (d) forming two phases, a first phase of the solvent and DMT, and a second phase of water, ethylene glycol, and catalyst.

DESCRIPTION OF THE DRAWINGS

For the purpose of illustrating the invention, there is shown in the drawings a form which is presently preferred; it being understood, however, that this invention is not limited to the precise arrangements and instrumentalities shown.

DESCRIPTION OF THE INVENTION

Figure 1:
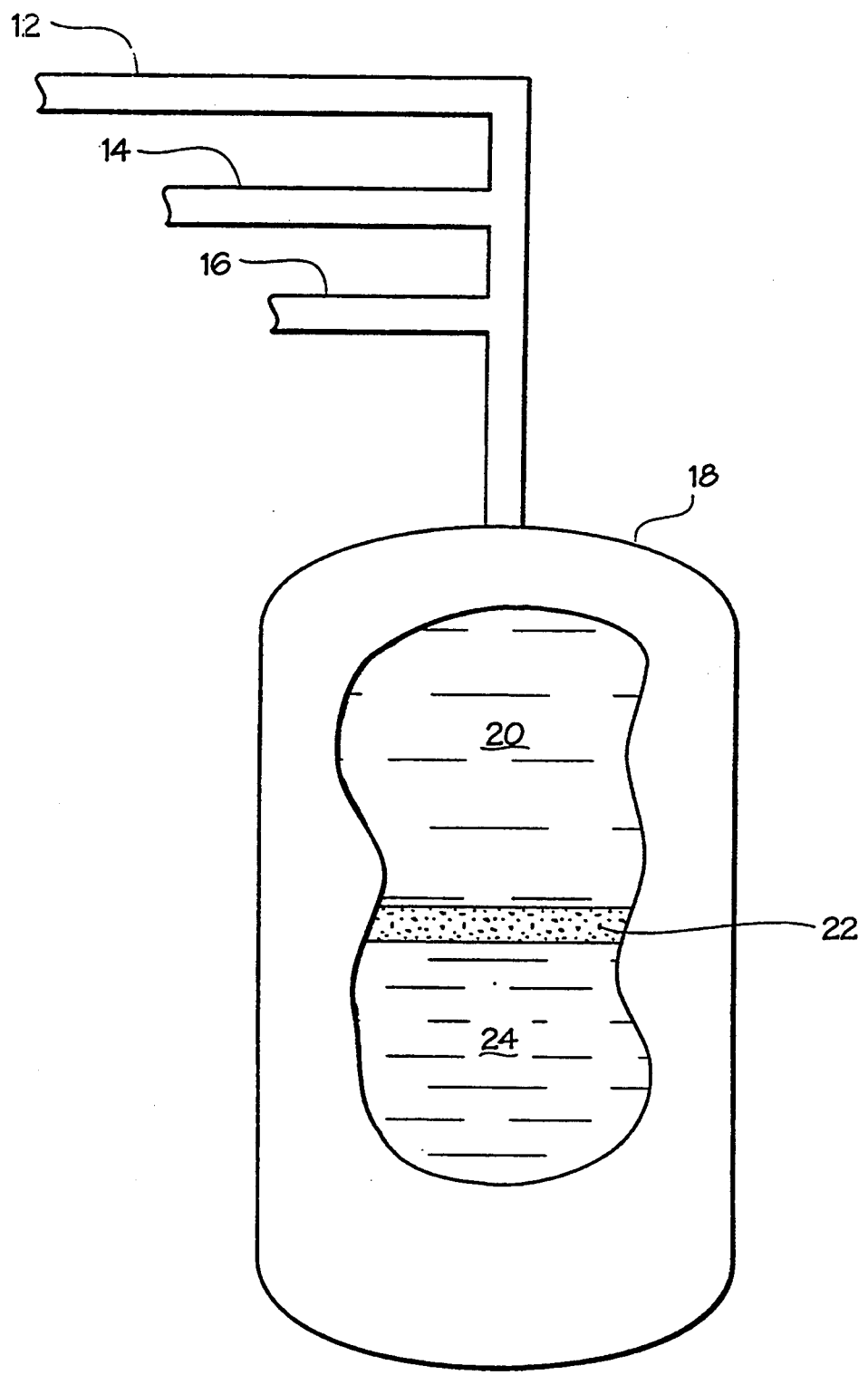
FIG. 1 is a schematic of the present invention, part broken away for clarity.

Referring to FIG. 1, there is shown a batch process for the recovery of DMT 10. An extractor 18 is charged with a DMT stream 12, a solvent stream 14, and a water stream 16. DMT stream 12 includes DMT, ethylene glycol (EG) and catalyst, as will be discussed below. In extractor 18, the feed streams, 12, 14, and 16, are mixed. After mixing, the liquid is allowed to settle and three distinct layers are formed within the extractor. Upper layer 20 is a solution of water and ethylene glycol. Bottom layer 24 is an organic solution of solvent and DMT. Middle layer 22 principally comprises the solid catalyst, but water is mixed therein.

Each layer, 20, 22, and 24, is removed from extractor 18, in any conventional fashion, and is further resolved, in any conventional manner. For example, the solutions of water/ethylene glycol and solvent/DMT may be conventionally resolved, e.g. via distillation, and the resulting components either directly recycled or further refined, in any conventional fashion. The mixture containing the catalyst can be recycled by known metallurgical processes.

Figure 2:
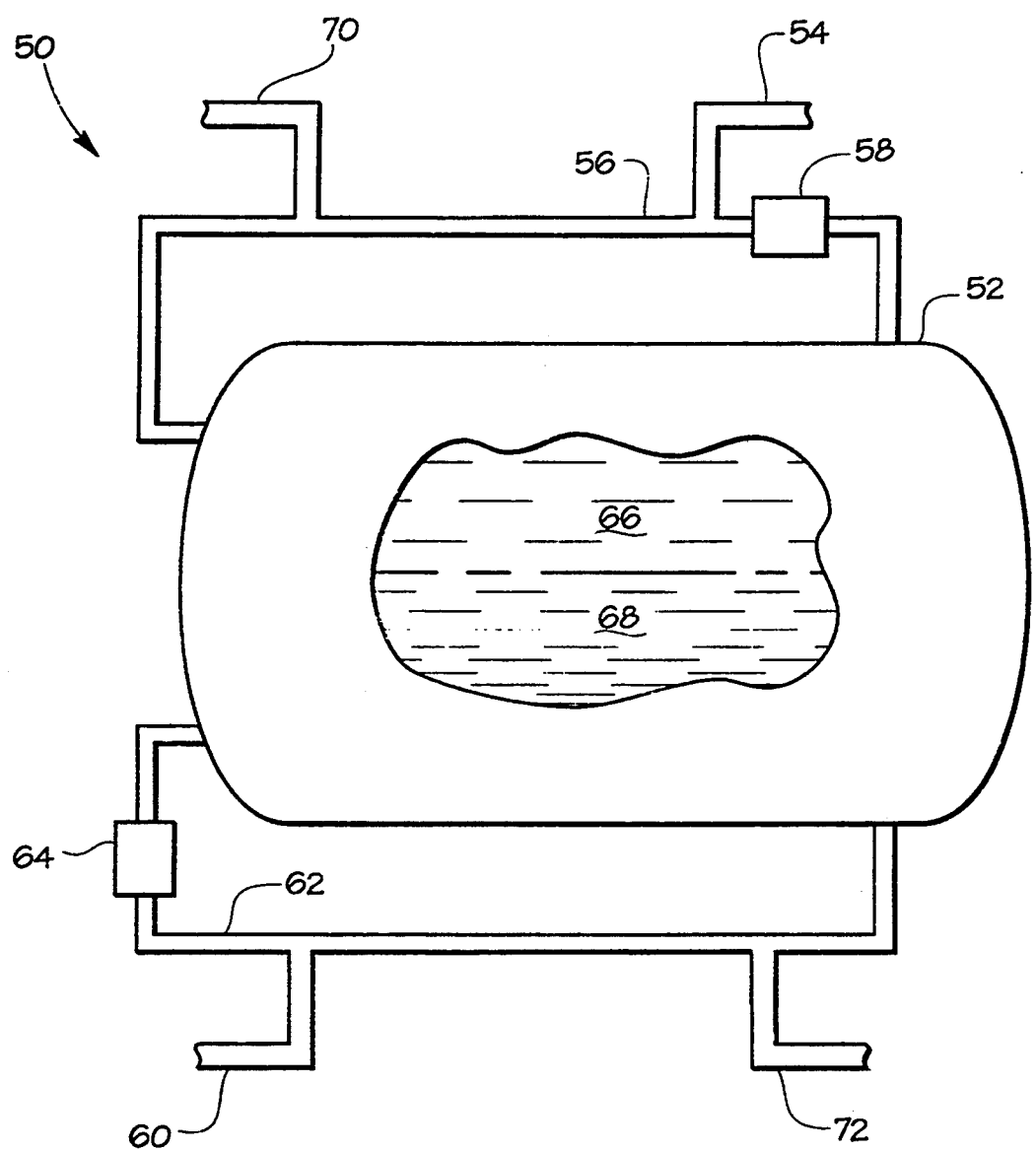
FIG. 2 is a schematic of an alternate embodiment of the present invention, part broken away for clarity.

Referring to FIG. 2, there is shown a continuous process for the recovery of DMT 50. The solvent stream and DMT stream are charged into extractor 52 via conduit 54 which is connected to an aqueous phase recycle line 56 and is passed through a conventional static mixer 58. The water stream is charged into extractor 52 via fresh water make-up line 60 which is connected to the organic phase recycle line 62 and is passed through a conventional static mixer 64. Within extractor 52, two phases are formed: an aqueous phase 66 and an organic phase 68. The aqueous phase 66 generally comprises water, EG, and catalyst. The organic phase 68 generally comprises solvent and DMT. The aqueous phase 66 is removed via conduit 70 which is connected to extractor 52 via aqueous phase recycle line 56. The catalyst, forming a part of aqueous phase 66, is subsequently and conventionally removed, e.g. by centrifuging. The organic phase 68 is removed via conduit 72 which is connected to extractor 52 via organic phase recycle line 62. The resulting streams, solvent/DMT, water/EG, and catalyst, are conventionally resolved into component parts, as discussed above.

The term "DMT stream" or "dimethyl terephthalate stream", as used herein, refers to a process stream containing, as the major components, DMT, ethylene glycol, and catalyst. The term "dimethyl terephthalate" or "DMT" also refers to partially reacted products from a preceding step where the scrap PET or PET production waste is converted to DMT, discussed below. These partially reacted products can pass through the process without adversely affecting the inventive process. These partially reacted products follow the DMT in the inventive process. The term "ethylene glycol" or "EG" also refers to higher glycols such as diethylene glycol and ethylene glycol. The term "catalyst" principally refers to the polycondensation catalyst from the PET polymerization, but may include catalyst from the preceding step of converting the staring materials to DMT (e.g., transesterification catalyst). The catalyst is most likely, but not necessarily, antimony (Sb)-based and may include manganese (Mn)-based, titanium (Ti)-based and/or germanuim-based catalysts. The DMT stream may comprise, by weight percent, about 40–70% DMT, about 60–30% EG, and about 0–3% catalyst.

Preferably, the stream comprises about 60% DMT, about 40% EG, and about 1% catalyst.

The source of the DMT stream is not critical, and it may be from scrap PET or PET production waste, e.g. from the ethylene glycol recovery unit associated with the polycondesation step of the PET polymerization (generally comprising about by weight about 70-30% BHET/oligomer and about 30-60% EG) or a combination of both. From either source, PET, BHET and/or oligomers (i.e., short chain or low molecular weight polymers formed from PET monomers) must be converted to DMT. The preferred conversion method is via reaction of the PET and/or BHET/oligomer with methanol, i.e. "methanolysis". Of course, any other method or combination of reactions could be used. Methanolysis is well known. For example, see U.S. Pat. Nos. 2,884,443; 3,037,050; 3,148,208; 3,321,510; 3,488,298; 3,907,868; 4,163,860; 4,578,502; and 5,051,528, each of which is incorporated herein by reference. If, after methanolysis, excess methanol is present, it should be removed, in any known fashion, from the DMT stream prior to the extractor. The DMT stream should have no more than 2% by weight methanol, but greater amounts can be tolerated by the process.

The term "extractor", as used herein, refers to a common chemical process vessel. For example, see Perry's, *Chemical Engineer's Handbook,* 5th Edition, McGraw-Hill Book Co., NYC, N.Y., 1973, p. 21-3-29, which is incorporated herein by reference. The extractor should be sized, in known ways, to handle the contemplated volume of materials. The extractor equipped with a mixer of sufficient capability intimately mixes the incoming streams. The time necessary for the formation of the layers or phases, will be dependent upon the volume of materials and specific process equipment utilized. The extractor may be a tank or other process equipment, e.g., a reciprocating extraction column. It is well known that proper selection of the process equipment can have benefical impact upon the process.

The term "solvent", as used herein, refers to any solvent that is immiscible with water and miscible with DMT. This solvent is perferrably an organic solvent. Exemplary solvents include: methyl benzoate; xylene; toluene; and methyl-p-toluate. The preferred solvent is methyl benzoate.

The term "water", as used herein, refers to any chemical process water stream.

In operation, the weight ratio of DMT stream/solvent/water should be within the range of about 1:0.5:0.5 to about 1:2:4, but the upper limit is constrained only by process economics. Preferably, the ratio is about 1:1:1. The process must be operated at a temperature where the DMT is soluble in the solvent, e g. with methyl benzoate above 80° C. preferably in that case, around 90°-100° C. As is well known to one of ordinary skill, variation of temperature and pressure can be used to modify the process without departing from the invention.

The invention will now be described in greater detail by way of the following non-limiting example.

EXAMPLE

A DMT stream containing DMT, ethylene glycol and antimony trioxide, in the amounts (grams as noted) listed in the table below, were added to a 500 mL beaker. Methyl benzoate, toluene, or xylene, as noted, were added and the mixture was heated (90° C.) until the solution was homogeneous, except for the antimony trioxide which is only slightly soluble in organic solvents. Water was added and the mixture was well agitated, then allowed to remain still, which resulted in two phases being formed, with the antimony trioxide settling to the bottom of the aqueous phase or remaining dispersed in the aqueous phase. Both the aqueous and the organic phases were analyzed and the results are listed in the table below. One additional extraction with water resulted in total removal of all the ethylene glycol from the organic phase.

TABLE

| RUNS | 1 | 2 | 3 | 4 | 5 | 6 | 7 | 8 | 9 |
|---|---|---|---|---|---|---|---|---|---|
| ANALYSIS OF CHARGE TO EXTRACTOR, GRAM ||||||||||
| DMT | 78 | 78 | 78 | 78 | 39 | 39 | 39 | 39 | 39 |
| EG | 51 | 51 | 51 | 51 | 51 | 51 | 51 | 51 | 51 |
| Sb | 2.15 | 2.15 | 2.15 | 2.15 | 0.36 | 0.36 | 0.36 | 0.36 | 0.36 |
| MeBenzoate | 132 |  | 132 | 264 | 132 |  |  | 132 | 264 |
| Toluene |  | 132 |  |  |  | 132 |  |  |  |
| Xylene |  |  |  |  |  |  | 132 |  |  |
| H20 | 132 | 132 | 264 | 132 | 132 | 132 | 132 | 264 | 132 |
| ORGANIC AND AQUEOUS PHASES, GRAMS ||||||||||
| ORGANIC PHASE ||||||||||
| DMT | 76 | 77 | 77 | 77 | 38 | 38 | 38 | 38 | 39 |
| EG | ND | 0.12 | 0.38 | 0.82 | 0.86 | 0.15 | 0.38 | 0.27 | 0.91 |
| Sb | NM | NM | NM | NM | 0.0041 | 0.0084 | ND | 0.0048 | ND |
| MeBenzoate | 130 |  | 131 | 263 | 129 |  |  | 131 | 262 |
| Toluene |  | 132 |  |  |  | 131 |  |  |  |
| Xylene |  |  |  |  |  |  | 131 |  |  |

NM = Not Measured
ND = Not detected
Sb = grams as elemental Sb, neglecting ligands The present invention maybe embodied in other specific forms without departing from the spirit or essential attributes thereof and, accordingly, reference should be made to the appended claims, rather than to the foregoing specification, as indicating the scope of the invention.

We claim:

1. A method for recovering dimethyl terephthalate comprised in the steps of:
   (a) providing a dimethyl terephthalate stream, the stream containing dimethyl terephthalate, catalyst, and ethylene glycol;
   (b) adding a solvent to the dimethyl terephthalate stream, the solvent being immiscible with water and miscible with dimethyl terephthalate;
   (c) adding water to the dimethyl terephthalate stream;

(d) forming two phases, a first phase of solvent and dimethyl terephthalate, and a second phase of water, dimethyl terephthalate ethylene glycol, and catalyst; and (e) recovering the dimethyl terephthalate from the first phase.

2. The method according to claim 1 wherein said solvent is selected from the group consisting of methyl benzoate; toluene; xylene; and methyl-p-toluate.

3. The method according to claim 1 wherein said solvent is methyl benzoate.

4. The method according to claim 1 wherein a weight ratio of dimethyl terephthalate stream to solvent to water is in the range of about 1:0.5:0.5 to about 1:2:4.

5. The method according to claim 1 wherein a weight ratio of dimethyl terephthalate to solvent to water is about 1: 1: 1.

6. The method according to claim 1 further comprising the step of resolving the catalyst from the solution of water and ethylene glycol.

7. A method for recovering dimethyl terephthalate comprising the steps of:
(a) providing a dimethyl terephthalate stream, the stream containing dimethyl terephthalate, catalyst and ethylene glycol;
(b) adding a solvent to the dimethyl terephthalate stream, the solvent being selected from the group consisting of methyl benzoate; toluene; xylene; methyl-p-toluate;
(c) adding water to the dimethyl terephthalate stream; wherein a ratio, by weight, of dimethyl terephthalate stream to solvent to water is in the range of about 1:0.5:0.5 to about 1:2:4;
(d) forming two phases, a first phase of solvent and dimethyl terephthalate, and a second phase of water, ethylene glycol, and catalyst; and
(e) removing the dimethyl terephthalate from the first phase.

* * * * *